United States Patent [19]

Van Driel et al.

[11] Patent Number: 5,859,366
[45] Date of Patent: Jan. 12, 1999

[54] STRAIN GAGE MEASUREMENT OF BLOOD VOLUME IN SOFT-SHELL VENOUS RESERVOIRS

[75] Inventors: Michael R. Van Driel, Fountain Valley, Calif.; Darren S. Gray, Grand Junction, Colo.; Victor C. H. Lam; Jill E. Uyeno, both of Honolulu, Hi.; Yu-Tung Wong, Huntington Beach, Calif.

[73] Assignee: Medtronic, Inc., Minneapolis, Minn.

[21] Appl. No.: 841,063

[22] Filed: Apr. 29, 1997

[51] Int. Cl.$^6$ ........................................................ A61B 6/00
[52] U.S. Cl. .................................................................. 73/149
[58] Field of Search .................................. 73/149, 290 R

[56] References Cited

PUBLICATIONS

Cobe Corporation Product Specification; Appendix C, pp. 46 & 47; date unknown.

*Primary Examiner*—Robert Raevis
*Attorney, Agent, or Firm*—Harry G. Weissenberger

[57] ABSTRACT

The blood volume contained in a soft-shell venous reservoir is measured by using strain gauges to detect variations in the expansion stress imposed upon the reservoir material or a film overlying the reservoir as the reservoir fills.

4 Claims, 2 Drawing Sheets

5,859,366

STRAIN GAGE MEASUREMENT OF BLOOD VOLUME IN SOFT-SHELL VENOUS RESERVOIRS

FIELD OF THE INVENTION

This invention relates to the measurement of the blood volume in a soft-shell venous reservoir of a heart-lung machine, and more particularly to a method and apparatus using stress variations in the shell of the reservoir to track blood volume variations.

BACKGROUND OF THE INVENTION

Heart-lung machines conventionally include a venous reservoir which receives the patient's blood at a variable rate during open-heart surgery and releases it at a substantially steady rate to the oxygenation circuit from which it is returned to the patient. In the operation of the heart-lung machine, it is important for the perfusionist to be continuously advised of the exact volume of blood in the reservoir, as this information is needed to maintain the correct diluted blood volume in the patient and to calculate the proper doses of infused drugs.

Rigid hard-shell reservoirs lend themselves well to this purpose because accurate graduations can readily be inscribed on their surface. However, because the volume of the hard-shell reservoir itself is constant, it will discharge potentially lethal air into the blood circuit of the heart-lung machine if it is allowed to become empty.

Collapsible soft-shell reservoirs (i.e. plastic bags) have the advantage of increasing and reducing their volume in accordance with the amount of blood they contain, and they consequently need no airspace that could produce emboli. On the other hand, soft-shell reservoirs, because they are always exactly filled with blood, cannot provide a visible volume indication by way of graduations.

In the past, perfusionists have estimated the blood volume in soft-shell reservoirs by the appearance of the reservoir bag, but this requires experience and is not sufficiently accurate for modern requirements. To remedy this deficiency, it has previously been proposed to position the reservoir bag between two parallel plates which are biased against the bag, and whose distance from each other is indicated by a tape measure. That system, however, is not very accurate and is awkward to observe.

SUMMARY OF THE INVENTION

The present invention fills the above-identified need by measuring the stress created in the bag material as a function of the expansion of the venous reservoir bag when it fills with blood. Any given bag design may be conventionally computer-modeled by finite element analysis to determine the areas of the bag material which are most stressed (i.e. bear the greatest load) upon expansion of the bag. Strain gages are then built into, or attached to, the bag material in those areas. Prior to use, the bag (or a representative sample of a production run) is calibrated by introducing known quantities of saline solution into the bag and recording the strain gage readings corresponding to those quantities. The data thus obtained is then interpolated by a microprocessor and translated into a digital volume readout.

DESCRIPTION OF THE PREFERRED EMBODIMENT

Figure 1:
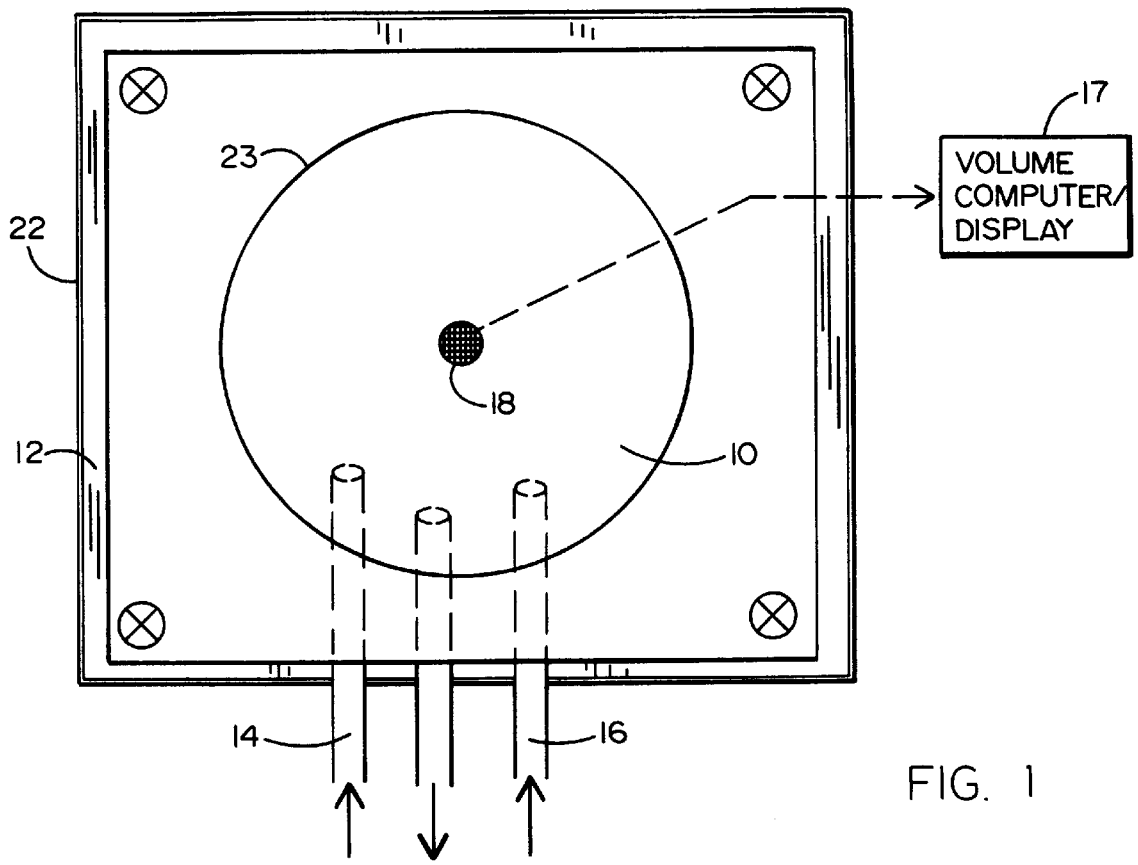
FIG. 1 is a schematic elevation of a first embodiment of the invention.
Figure 2:
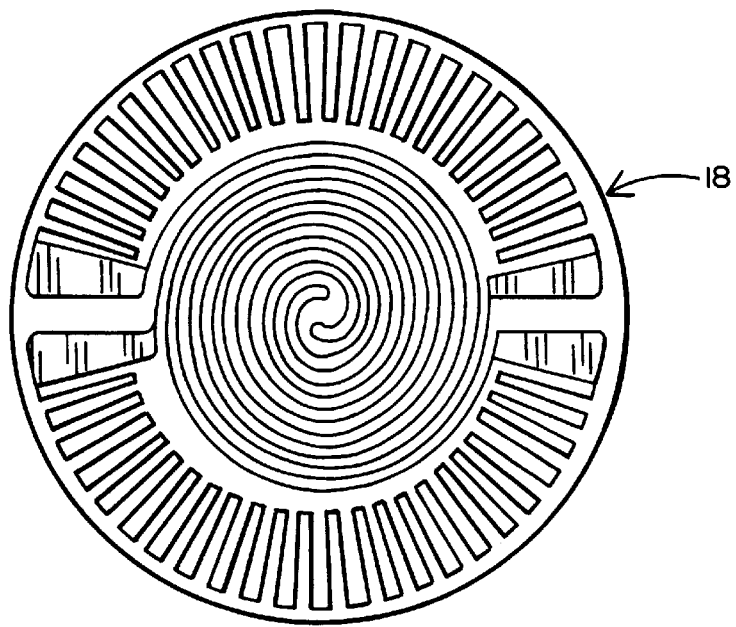
FIG. 2 is a plan view of a diaphragm strain gage useful in the embodiment of FIG. 1.

FIG. 1 shows the invention in its simplest form, based on the assumption that the material of a venous reservoir bag 10 firmly mounted on a backplate 12 is stressed most strongly at its center when the bag 10 expands as it fills with blood from the venous inlet 14 and the cardiotomy inlet 16. The stress at that point is advantageously measured by a diaphragm strain gage such as the conventional gage 18 depicted in detail in FIG. 2. It should be understood that the above assumption may not hold true for all designs of venous reservoir bags. However, the points of maximum stress can be conventionally computed for any given design by finite element analysis, and strain gages can be applied at the points thus determined. The stress measured by the gage 18 can be empirically related to the volume of the bag 10 by measuring the stress created by a known quantity of blood in a representative sample of a given bag design, and using that information (e.g. by way of a look-up table or microprocessor program) to program a volume computer/display 17 to digitally display the blood volume.

Figure 3:
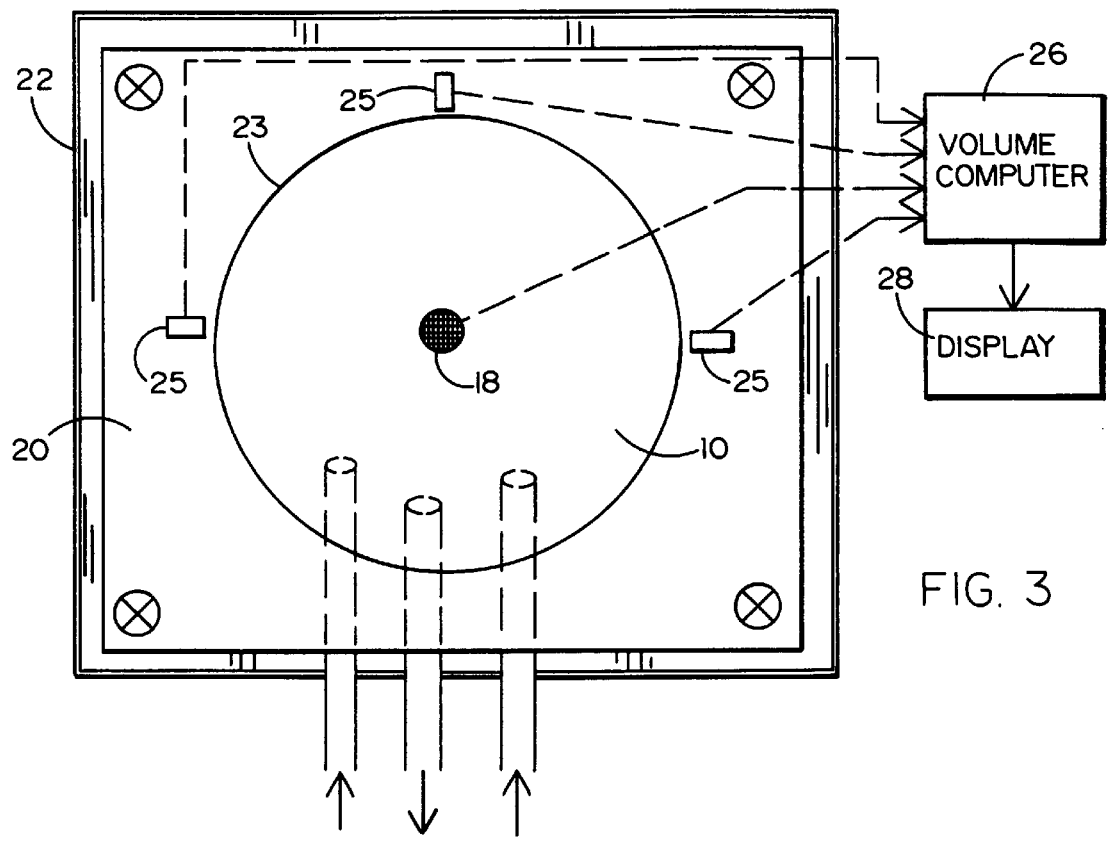
FIG. 3 is a schematic elevation of a second embodiment of the invention.

FIG. 3 illustrates a more sophisticated embodiment of the invention. In that embodiment, the reservoir bag 10 is formed in a flexible plastic sheet 20 which is secured on all four of its sides to a backplate 22. The flexible sheet 20 may preferably consist of two layers of plastic which are welded together between the backplate 22 and the edge 23 of the bag 10. Inside the edge 23, the two layers are separable to form the bag 10. General purpose strain gages 25 (which are less sensitive but also less expensive than the diaphragm gage 18) are firmly embedded between the two layers of sheet 20 so as to record the stress pattern therein. Optionally, a diaphragm strain gage 18 may also be placed on the outside of the reservoir 10 at its center.

The placement of the strain gages 25 is so chosen, as shown in FIG. 3, that they will be exposed to the greatest strain upon expansion of the reservoir 10. Because of the movement of the walls of reservoir 10 away from each other, the strain is greatest near the circular edge 23. Also, the pulling strain per cm on gages 25 is greatest where the distance between the edge 23 and the backplate 22 is smallest.

As in the embodiment of FIG. 1, the readings of the strain gages 18 and 25 are applied to a microprocessor or volume computer 26 which is empirically programmed to translate the strain gage readings into a reservoir volume indication that can be digitally displayed on a display 28.

Figure 4:
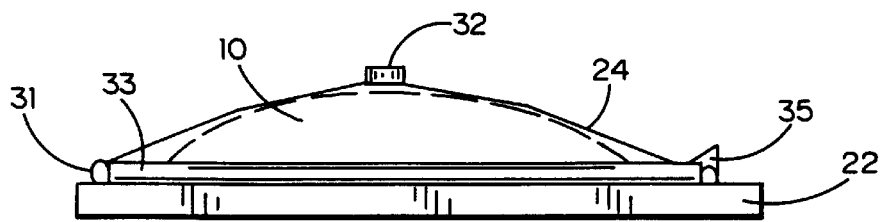
FIG. 4 is a horizontal section of a third embodiment of the invention.

A third embodiment of the invention is shown in FIG. 4. In that horizontal section (the corresponding elevation would be essentially the same as FIG. 3), a plastic film 24 is so attached to a frame 33 hinged at 31 to the backplate 22 that it can be swung into intimate contact with the bag 10 about the hinge 31 after the bag 10 has been mounted on the backplate 22. In the embodiment of FIG. 4, the strain gage 32 is mounted on the film 24. The film 24, which is preferably resilient, deforms and gets stressed in the same manner as the bag 10, but it does not need to be disposable as the bag 10 must be. Substantial cost savings as well as greater stress sensitivity are thus realized.

It is understood that the exemplary strain gage measurement of blood volume in soft-shell venous reservoirs described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A system for measuring the blood volume in a expandable soft-shell venous reservoir, comprising:

a) a rigid backplate;

b) a soft-shell venous reservoir planarly mounted on said backplate;

c) at least one strain gage so positioned with respect to said reservoir as to produce an electrical signal in response to an expansion strain in the material of said soft-shell reservoir, said reservoir being formed by a pair of plastic sheets which are bonded to each other in a peripheral area but separable in a central area to form an expandable blood container, and in which a plurality of strain gages are bonded to said sheets in said peripheral area.

2. The system of claim 1, in which the periphery of said sheets is substantially rectangular, said central area is substantially circular, and said strain gages are disposed substantially on lines along which the distance between said periphery and said central area is smallest.

3. A system for measuring the blood volume in an expandable soft-shell venous reservoir, comprising:

a) a rigid backplate;

b) a soft-shell venous reservoir planarly mounted on said backplate;

c) a frame;

d) a deformable film mounted in said frame and carrying at least one strain gage arranged to produce a signal representative of deformation stress in said film;

e) said frame being so movable with respect to said backplate as to bias said sheet into contact with said reservoir throughout the expansion thereof; and d) apparatus arranged to compute and display the blood volume in said reservoir by electrically comparing said signal with signals produced by known volumes of blood in said reservoir.

4. The system of claim 3, in which said frame is hinged to said backplate.

* * * * *